United States Patent [19]
Schmidt

[11] Patent Number: 5,830,859
[45] Date of Patent: Nov. 3, 1998

[54] COMPLEX FOR INDUCING BONE GROWTH IN THE MAXILLARY SINUS

[76] Inventor: Karlheinz Schmidt, Aeussol Weitesg.12, 72810 Gomaringen, Germany

[21] Appl. No.: 473,878

[22] Filed: Jun. 7, 1995

Related U.S. Application Data

[63] Continuation-in-part of Ser. No. 350,666, Dec. 7, 1994, abandoned, which is a continuation of Ser. No. 844,083, Mar. 2, 1992, abandoned.

[51] Int. Cl.⁶ ....................................................... A61F 2/28
[52] U.S. Cl. ................................. 514/12; 514/21; 514/56; 530/356; 424/422; 424/484
[58] Field of Search ........................ 514/12, 21; 424/422, 424/484; 530/356, 399; 574/56; 623/16, 18, 66

[56] References Cited

U.S. PATENT DOCUMENTS

| | | | |
|---|---|---|---|
| 4,950,483 | 8/1990 | Kszndoz et al. | 424/422 |
| 5,024,841 | 6/1991 | Chu et al. | 424/422 |
| 5,556,430 | 9/1996 | Gendler | 623/16 |

*Primary Examiner*—Cecilia J. Tsang
*Assistant Examiner*—Patrick R. Delaney
*Attorney, Agent, or Firm*—Wigman, Cohen, Leitner & Myers, P.C.

[57] ABSTRACT

A protein complex for inducing growth of bone in the maxillary sinus of an animal is disclosed. The complex is generally made from animal bone, defated, demineralized, ground, slurried, and fractional such that functional structural, adhesive, chemotaxis, and growth components are isolated and purified.

11 Claims, 6 Drawing Sheets

COMPLEX FOR INDUCING BONE GROWTH IN THE MAXILLARY SINUS

CROSS-REFERENCE TO RELATED APPLICATION

This is a continuation-in-part of application Ser. No. 08/350,666 filed Dec. 7, 1994, now abandoned which is a continuation of application Ser. No. 07/844,083 filed Mar. 2, 1992 now abandoned, both incorporated herein by reference. Also incorporated by reference is my co-pending application entitled "Complex for Inducing Bone Growth in the Mastorial Cavity" filed concurrently herewith.

FIELD OF THE INVENTION

The present invention relates generally to a complex or material capable of stimulating new bone growth and, more particularly, to the use of this complex to reossify the maxillary sinus.

BACKGROUND OF THE INVENTION

Dental patients confronting tooth loss, in particularly the elderly, often seek alternatives to dentures. While implants can function as denture alternatives, anchoring the implant is often difficult because the maxilla may be too thin to strongly support the artificial tooth. It would be desirable, therefore, to have a method for building-up or thickening the maxilla. Such a method would also be useful in treating jaw bones damaged by trauma or tumors.

Most of the knowledge gained in the last 20 years regarding "induced bone growth" is based on animal testing conducted by Urist. See Dubuc FL, Urist MR (1967): The accessibility of the bone induction principle in surface decalcified bone implants. Clin Orthop 55: 217–224; Glowacki J. Altobelli D, Mulliken J B (1981): Fate of mineralized and demineralized osseous implants in cranial defects. Calcif Tissue Int 33: 71; Glowacki J. Kalban L B, Murray J E, Folkmann J, Mulliken J B (1981): Application of the biological principle of induced osteogenesis for craniofacial defects. Lancet 1: 959–962; Holz U, Thielemann F W, Herr G, Pfleiderer G (1985): Osteoinductive bone matrixextracts; Huggins C B, Wiseman S, Reddi A H (1970): Transformation of fibroblasts by allogenic and xenogenic transplants of demineralized tooth and bone. J Exp Med 132: 1250–1258; Koskinen E V S, Ryoppy S A, Lindholm T S (1972): Osteoinduction and osteogenesis in implants of allogenic bone matrix. Clin Orthop 87: 116–131; Mulliken J B, Glowacki J, Kaban L B, Folkmann J, Murray J E (1981): Use of demineralized allogenic bone implants for the correction of maxillocraniofacial deformities. Ann Surg 194: 366–372; Urist M R, Dowell T A, Hay P H, Strates B S (1968): Inductive substrates for bone formation. Clin Orthop 59: 59–96.

It has been demonstrated that the "osteogenic activity of the bone" is determined by a protein component of the bone matrix called a "bone morphogenetic protein" (BMP). See Urist M R, Iwata H (1973): Preservation and biodegradation of the morphogenetic property of bone matrix. J Theor Biol 38: 155–167; Urist M R, Mikulski A, Conteas (1975): Reversible extintion of the morphogen in bone matrix by reduction and oxidation of disulfide bonds. Calcif Tissue Res 19: 73–83. After extraction by means of a 0.5 molar calcium dichloride 6 molar urea solution in various purification steps, Urist characterized the BMP (=b–BMP), which was obtained from beef bones. He described it as an acidic, non-collagenic protein with obviously essential disulfide bonds and a relative molecular weight of 18.5 kDa. These disulfide bonds were essential since no further splitting of the protein was possible after chemical reduction by electrophoresis, without losing the osteogenic activity of the extract. After limited proteolysis by pepsin and trypsin, (See Urist M R, Iwata H, Cecotti P W L, Dorfman R L, Boyd S D, McDowell R M, Chien C (1973): Bone morphogenesis in implants of insoluble bone gelatine. Proc Nat Acad Sci USA 70: 511–3515) the isolation of osteoinductive subunits with relative molecular weights of between 4 and 7 kDa was later achieved.

An intramuscular heterotopic bone formation could be triggered with mg portions of the purified protein complex in rats. Wang et al. isolated a transformed growth factor (TGFB) with osteogenic activity from the beef bone after a 300,000 fold, 7 step comprehensive chromatographic purification. See Wang E A, Rosen V, Cordes P, Hewick R M, Kriz M J, Luxenberg D P, Sibley B S, Wozney J M (1988): Purification and characterization of other distinct bone-inducing factors. Proc Natl Acad Sci USA 85: 9484–9488. Although the main portion of this factor is demonstrated in thrombocytes (PDGF), it could be isolated in acceptable quantities from bone as well. He could demonstrate that this growth factor from osteocytes, obtained from cow bones, was produced and a share of high quantity was given to the formation and the remodelling of the bone.

The relative molecular weight was set by means of sodium dodecyl sulfate polyacrylamide gel electrophoresis (SDS-PAGE) under non-reduced conditions of 30 kDa.

After reduction, inactive BMP subunits of 30, 18 and 16 kDa were found. All BMP groups possessed sugar groups, since the relative molecular weights were lessened after glygogenase treatment. Wang could induce in-vivo bone and cartilage with quantities of the purified factor by using inactive rat bone matrix as the biological carrier.

Sampath et al. isolated an in-vivo bone growth induced protein from beef bone, which he called "osteogenin". See Sampath T K, Muthukumaran N, Reddi A H (1987): Isolation of osteogenin, an extracellular matrix-associated, bone-inductive protein, by heparin affinity chromatography. Phy Proc Natl Acad Sci USA 84: 7109–7113

Its molecular weight is approximately 22 kDa according to SDS-PAGE, but was later corrected to a weight of between 30 and 40 kDa.

Likewise, the bone induction in subcutaneous implants succeeded after using an inactive bone matrix as a carrier with 1–5 ug of the purified protein. The comparison of the amino acid sequences allows a considerable similarity to Wang's BMP to be expected. The exact assembly of b-BMP is still not known. Although the authors noted above worked with a purity factor of about 300,000, the protein complex with a relative molecular weight of 30–40 kDa found by WANG appears to be the closest. See Luyten F P, Cunningham N S, Ma S, Muthukumaran N, Hammonds R G, Nevins W B, Wood W I, Reddi A H (1989): Purification and partial amino acid sequence of osteogenin, a protein initiating bone differentiation. J Biol Chem 264: 13377–13380. The cause for the different activity of various BMP's, measured with the help of semi-quantitative histological criteria, appears to lie in the use of different carrier materials.

The results from Urist, Wang and Sampath can not necessarily be compared with the results of other groups, since their reports frequently refer to the use of raw bone extract with a very low activity, and these results probably can be traced back to unfavorable immune reactions against BMP subunits. Other authors use animals with artificially produced immune sufficiency and thus demonstrate high activity, even for raw BMP extracts.

On the other hand, Urist obtained the purity and isolation of human BMP (h15 BMP) from cortical bone matrix and various osteo-sarcomas. After spinal chromatography and preparative gel electrophoresis (See Urist M R, Sato K, Brownell A G, Malinin T I, Lietze A, Huo Y, Prolo D J, Oklund S, Finerman G A M, DeLange R J (1983): Human bone morphogenetic protein (hBMP). Proc Soc Biol Med 173: 194–199), he achieved the isolation of a relatively insoluble, acidic protein with a relative molecular weight of 17.5 kDa. Furthermore, it required a "supramolecular aggregate," composed of non-osteogenic matrix proteins which imparts the osteogenic activity of the h-BMP to the target cells. With mg quantities of the purified protein, bone formation could be caused in rat muscle.

In 1988, Wozney achieved the isolation of three complementary DNA clones from different human cell lines in the USA, which coded three different proteins. These proteins were characterized thoroughly by him and referenced as BMP-1, BMP-2 and BMP-3 (40). He reported the complete amino acid sequence of three human pro-BOP's, derived from the DNA code he isolated before. BOP-1 was characterized as a multi-area regulatory protein, whose precursor, pro-BOP 1 is comprised on 730 amino acids.

The subunits BOP 2a, BOP 2b and BOP 3 were described as parts of a multifunctional growth factor (TGF). For pro-BOP 2a, an amino acid sequence length of 396 amino acids was given, whereas pro-BOP 2b is made up of 408 and pro-BOP 3 of 472 amino acids. It was managed to isolate and purify active BOP-1, BOP-2a and BOP-3 fractions by using the protein synthesis apparatus from hamster ovaries and E.Coli branchia by means of heparin affinity chromatography.

In animal testing, it could be demonstrated that all recombined h-BOP fractions were individually in the position to cause the formation of cartilage 7 days after implantation in young rat muscle. Data from long-term tests were not presented, so that the bone-inducing activity of these h-BOP's remain to be demonstrated. He concluded from his results, assuming that these isolations are really bone-inducing factors, that there are some different osteoinductive proteins in the human bone matrix, similar to in the beef bone matrix. The difference between the pro-BOP fractions and the mature BOP fractions, as well as the exact amino acid sequence of the mature h-BMPs is currently not known.

Porcine BOP is characterized currently as a non-collagenic protein with a relative molecular weight of >17.5 kDa. It demonstrates a high activity, measured 25 days after the implantation in the abdominal muscle of immune supplemented, male grown Wistar rats. Half the activity could be demonstrated on non-immune supplemented rats (41). Meanwhile, after the osteogenic activity for bovine, human and porcine BOP factors could be demonstrated in rats, it can be concluded that the effect is not species-specific. Analyses followed in which the osteo-inductive potential of other known growth factors was examined. Thus the growth factor PDGF derived from thrombocytes, for example, the human epidermal growth factor h-EGF, the human transforming growth factor TGF, the fibroblast growth factor FGF, the skeletal growth factor SGF, Interleukin-1, the bovine growth hormone BSH and other peptide factors were analyzed for their bone growth inducing properties.

In-vitro chondrogenesis and cartilage specific proteoglycansynthesis in rat muscle cultures can be caused with some of these factors.

Other extracts from the connective tissue matrix, which were appropriately manufactured in the BOP extraction process, showed no osteogenic activity. From this it can be concluded that the bone growth factor induced effect is a one-time biological property of BOP. A central problem in obtaining BOP lies in the unusual physiochemical properties of the starting material, the bone. This must be converted to a bone matrix, free of fat, water and bone minerals before the BOP extraction, while maintaining the activity. The starting material must be freed of attached soft tissue and cleaned of marrow. Subsequently, it is crushed into 1 mm pieces when frozen and subjected to demineralization, fat removal and freeze drying. These steps require a large amount of bone material and mean a substantial time expenditure. Only about 20–30% of the bone is composed of organic matrix. Since BOP is bound by strong non-covalent forces, extreme extraction techniques are required.

These forces were broken by strongly denaturing "salting in" electrolytes, such as guanidine hydrochloride in high concentrations. See Arakawa T, Timasheff S N (1984): Protein stabilization and destabilization by guanidinium salts. Biochemistry 23: 5924–5929; Joly M (1965): A physio-chemical approach to the denaturation of proteins. In: Horecker B, Kaplan No, Scheraga H A (eds): Molecular biology, Vol 6 Academic Press, London New York, pp 1–342; Tanford C (1968): Protein denaturation. Part A. characterization of the denatured state. Adv Protein Chem 23: 121–217; Tanford C (1968): Protein denaturation. Part B: the transition from native to denatured state. Adv Protein Chem 23: 218–282; Tanford C (1969): Protein denaturation. Part C: theoretical models for the mechanism of denaturation. Adv Protein Chem 24: 1–95.

During the denaturing phase which lasts about 16 hours, the solvent slowly penetrates the thick structure of the collagenic matrix. The size of the particles of original material, the extraction time as well as the ratio of solvent to matrix can significantly influence the yield. The now present "raw extract" comprises a complex mixture of soluble collagens and various non-collagenic proteins which are only difficult to fractionate. During the entire purification, dissociated conditions are required. These are achieved by using a 4 molar guanidine hydrochloride or 6 molar urea solution. At concentrations which are too low, BOP tends to establish and break bonds with other matrix proteins. The osteogenic potential of the BOP fractions isolated in this way are usually tested with the help of an in-vivo trial. The substrate is implanted at a point on the outside of the skeletal system on the appropriate test animal. In-vitro tests have proved to be insufficiently specific.

The quantity and the quality of the newly formed bone is influenced by various physiochemical factors. See Urist M R (1989): Bone morphogenetic protein induces bone formation and the bone-bone marrow consortium. In: Aebi M, Regazzoni P (eds): Bone transplantation. Springer, Heidelberg New York, pp 185–197.

The activity of the implant depends directly on the osteogenic potential of the recipient animal and the type of implantation. See Urist M R, Hay P H, Dubuc F, Buring K (1969): Osteogenic competence. Clin Orthop 64: 194–220.

The potential is very high for rodents, above all after intramuscular implantation.

Furthermore, the age of the recipient animal plays a significant roll. Older animals show a clearly reduced activity with regard to the induced bone formation. See Irving J T, LeBolt S A, Schneider E L (1981): Ectopic bone formation and aging. Clin Orthop 154: 249–253.

Similar is true for the osteogenic activity in regard to the age of the donor animal. See Reddi A H (1985): Age dependent decline in extracellular matrix-induced local bone differentiation. Isr J Med Sci 21: 312–313.

Specific and unspecific immune rejection reactions of the recipient are likewise meaningful for the osteogenic effect.

As mentioned, the inactivity or the low activity of the raw bone extracts can be traced back to strongly immunologically effective components of this kind of implant. See-Luyten F P, Cunningham N S, Ma S, Muthukumaran N, Hammonds R G, Nevins W B, Wood W I, Reddi A H (1989): Purification and partial amino acid sequence of osteogenin, a protein initiating bone differentiation. J Biol Chem 264: 13377–13380

For this, the specific cell caused immune reactions have the greatest meaning. This could be proven by comparative studies of immune supplemented rats. A complete loss of activity in untreated rats occurred after using impure extract, whereas a high osteogenic activity of the same extract was to be noted in animals which were treated immunosuppressively beforehand with Cyclosprin A. After each successive purification step, the activity loss of the extract could be reduced in the untreated recipient animals. From this it can be concluded that the immunogenic properties of the implants could be ascribed to the impurity of the extract with high molecular weights.

However, unspecific rejection factors, as for example, extracellular, proteolytic or phagocytic reactions after traumatization of the implant area, lead to a loss of activity of the implant. This is concluded from observations made of immunsuppremated animals which were bilaterally treated, which subsequently formed quantitatively different quantities on the bone substance. See Aldinger G, Herr G, K üsswetter W, Reis H J, Thielemann F W, Holz U (1991): Bone morphogenetic protein: a review. Int. Orthop 15: 169–177.

A comparative view of the results of different research groups is very difficult. The main differences consist in the use of different donor animals, different recipient animals, test animals with different immune status, different ages as well as different types of implants.

The test duration varies for the individual authors as well. As an example, the calcium content of the explanted tissue is noted. This increases with additional maturity and mineralization of the newly formed bone. It turns out to be difficult to quantify the newly formed material, since the authors used different methods for determining the mass of bone. The activity of the alkaline phosphatase (AP), for instance, the calcium content, the ash weight and the 45 Ca activity of the explanted tissue are referenced as biochemical factors.

Furthermore, the quantitative end result is influenced by the use of suitable carrier substances, which are to be seen as BOP-retarding-freeing delivery systems. See Aldinger G, Herr G, Küsswetter W, Reis H J, Thielemann F W, Holz U (1991): Bone morphogenetic protein: a review. Int. Orthop 15: 169–177

Different organic and inorganic carrier systems were used with varying results, thus, for example, human Type-1 collagen, human fibrin, inactive bone matrix, gypsum, β tricalcium phosphate and hydroxyapatite in connection with collagen. See Deatherage J R, Miller E J (1987): Packing and delivery of bone inducting factors in a collagenous implant. Coll relat Res 7: 225–231; Kawamura M, Urist M R (1988): Human fibrin is a physiologic delivery system for bone morphogenetic protein. Clin Orthop 235: 302–310; Yamazaki Y, Oida S, Akimoto Y, Shioda S (1988): Response of the mouse femoral muscle to a composite of bone morphogenetic protein and plaster of paris. Clin Orthop 234: 240–249

In general, it can currently be said that BOP can be described as a paracrinic, proteohormone-similar factor, whose effect on the point of its implantation is limited. The bone formation caused in this way represents a complex cell differentiation process. See Reddi A H (1981): Cell biology and biochemistry of endochondral bone development. Coll. Relat Res 1: 209–226

With regard to the use of BOP on higher vertebrate animals, there are only a few reports. FERGUSON et al. report on a test model, in which artificially produced defects of a specific diameter on the skull of Rhesus monkeys were treated with bovine BOP. The defects were arranged so that they could not heal in the normal life span of the animals. He reports a complete regeneration of defects of 14 to 20 mm, which had been treated with b-BOP. See Ferguson D, Davis W L. Urist M R, Hurt W C, Allen E P (1987): Bovine bone morphogenetic protein (b BMP) fraction induced repair of craniotomy defects in the rhesus monkey. Clin Orthop 219: 251–258.

He compared the healing with contralateral defects in animals which contained only beef albumin. Similar tests were conducted with grown sheep. Defects of 18 to 20 mm healed completely in all animals with new bone formation. See Lindholm T C, Lindholm T S, Alitalo I, Urist M R (1988): Bovine bone morphogenetic protein induced repair of skull trephine defects in sheep. Clin Orthop 227: 265–268.

Test conducted on dogs and rats in regard to this confirm this study. See Sato K, Urist M R (1985): Induced regeneration of calvaria by bone morphogenetic protein in dogs. Clin Orthop 187: 301–311. BOP implants in diaphyseal defects in dogs were less successful since only one fibrous healing took place. See Johnson E E, Urist M R, Schmalzried T P, Chotivichit A, Huang H K, Finerman G A M (1989): Autogenic cancerous bone grafts in extensive segmental ulnar defects in dogs. Clin Orthop 243: 254–265.

BOP fractions, which had been implanted in the cervical muscle of sheep and dogs, as well as in the subcutaneous tissue of people, could induce no heterotopic bone formation.

This was traced back to immunologically effective impurities, to lacking carrier preparations and other adverse test factors. See Lindholm T C, Lindholm T S, Alitalo I, Urist M R (1988): Bovine bone morphogenetic protein induced repair of skull trephine defects in sheep. Clin Orthop 227: 265–268

With regard to the clinical application, there are currently three preliminary reports on the treatment of large bone defects with BOP.

In the first report, 12 patients with established non-connection of the femur shaft received autogenic or foreign transplants with a BOP preparation which is only partially purified. In 11 of 12 cases, a bony unification could be achieved after an average healing period of 4.7 months. See Johnson E E, Urist M R, Finerman G A M (1988): Bone morphogenetic protein augmentation grafting of resistant femoral nonunions. Clin Orthop 230: 257–265.

In addition, 6 patients with segmental tibia defects in lengths of 3 to 17 cm were reported. After implanting h-BOP and autologous bone transplants, healing could be achieved in all the cases. See Johnson E E, Urist M R, Finerman G A M (1988): Repair of segmental defects of the tibia with cancellous bone grafts augmented with human bone morphogenetic protein. Clin Orthop 236: 249–257. Also, h-BOP was used successfully in filling a defect on a hand, caused by an ecchondroma. See Urist M R, Kovacs S, Yares K A (1986): Regeneration of an enchondroma defect under the influence of an implant of human bone morphogenetic protein. J Hand Surg 11A: 417. These methods noted above yield often only a "moderately satisfactory" to "poor" result.

SUMMARY OF THE INVENTION

The present invention relates to a bone inducing protein complex ("BIC") as an implant in the area of the maxillary sinus. As used herein, the term "BIC" means complex or bone inducing protein complex; the term "HA" means hydroxy apetite.

Efficacy is demonstrated by a suitable animal model—pigs. On one side of the pig's face a cavity in the maxilla is filled with BIC protected by a lattice-work made of titanium. On the opposite side of the pig's face a corresponding cavity served as a control.

After implantation of BIC as lyophilisate and hydroxyapatite ceramic as grains in the area of the maxillary sinus in ten pigs, BIC or hydroxyapatite ceramic were found to induce bone growth only after a dimensionally stable cavity was created to protect the implants from the resorptive forces of the mucus membrane of the maxillary sinus and where sufficient large quantities of BIC or HA were used. Twelve or eight weeks after the operation, the following results could be summarized.

In all the test animals, a complication-free recovery took place after the implantation of BIC as well as hydroxyapatite ceramic in the area of the maxillary sinus. No postoperative complications caused by the operation were observed in any of the cases. The titanium grid used in the second part of the testing was likewise integrated without reaction in the bones or tolerated by the mucus membrane in the maxillary sinus. It could be demonstrated that under certain conditions, the implantation of BIC induced the formation of a well-differentiated lamellar bone. The quantity of BIC used must be sufficient to effect a signal effect on the appropriate cell system, besides implanting it in a dimensionally stable cavity.

In contrast to this, in the area of the HA ceramic, a connective tissue healing of the implant took place, however, a new formation of bone could not, or only in small quantity, be observed.

With the foregoing and other objects, advantages and features of the invention that will become hereinafter apparent, the nature of the invention may be more clearly understood by reference to the following detailed description of the invention, the appended claims and to the several view illustrated in the attached drawings.

DETAILED DESCRIPTION OF THE INVENTION

Figure 1:
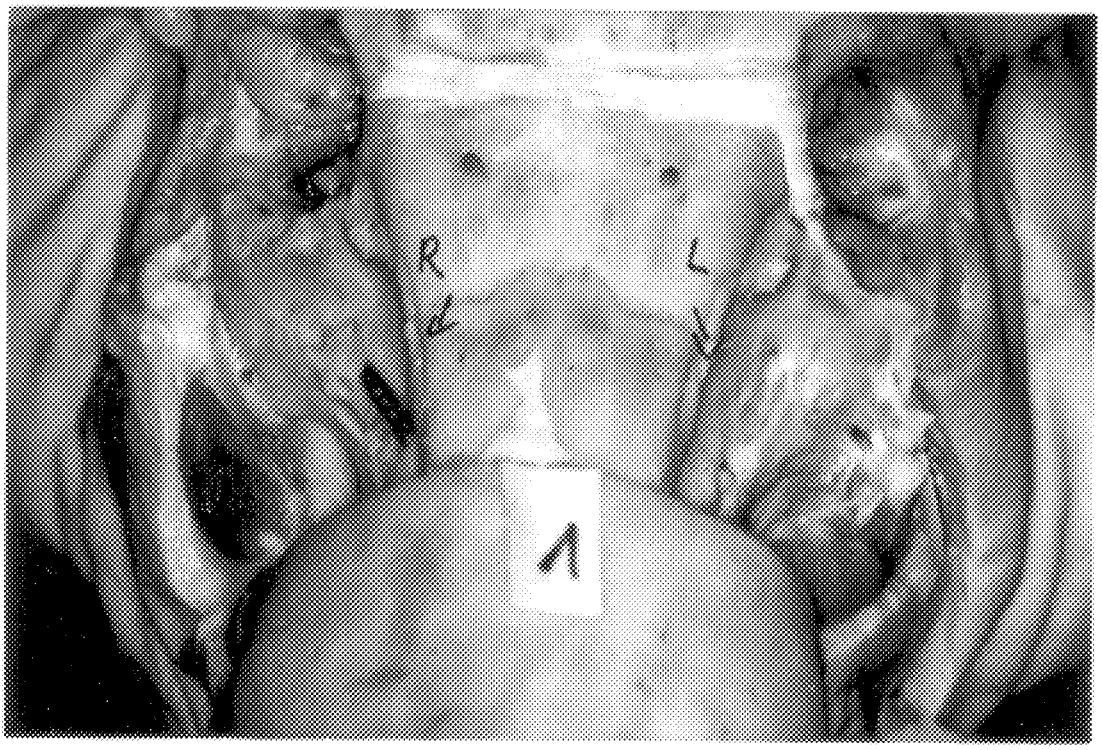
FIG. 1 is a photograph showing the crease of the titanium grid integrated in the side upper maxillary sinus bone.
Figure 2:
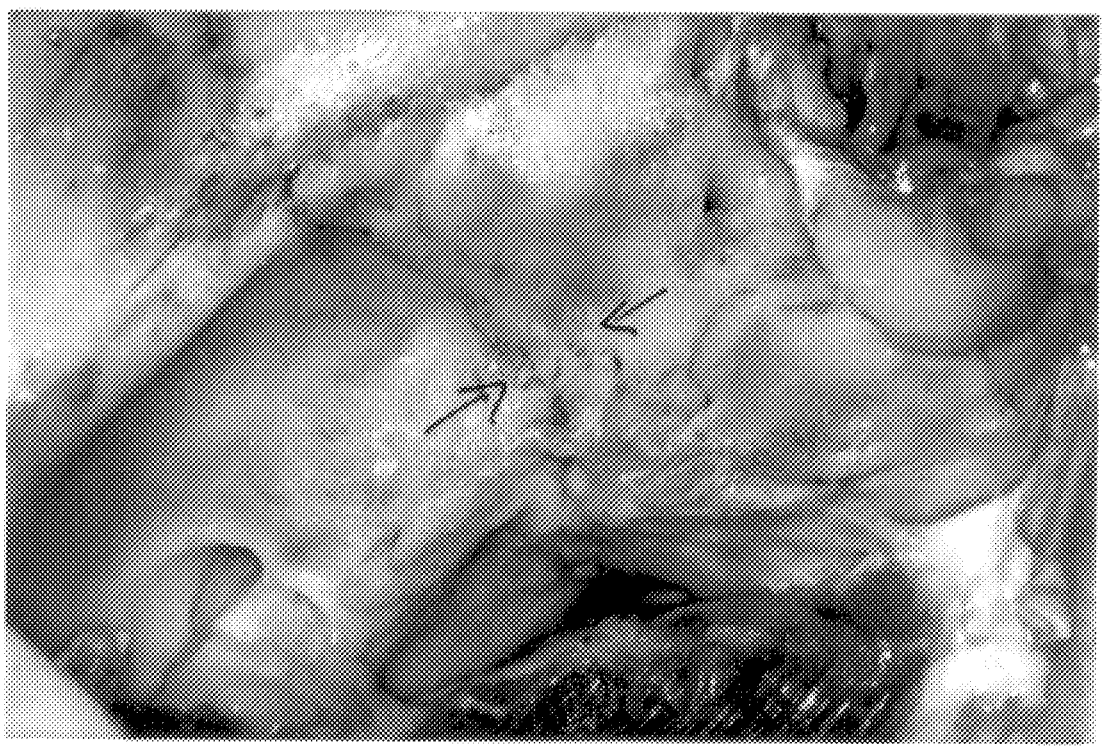
FIG. 2 is a photograph showing the titanium grid shining through bluish, almost completely covered in bone. In comparison to FIG. 1, a distinct new formation of bone which exceeds normal healing is visible.
Figure 3:
FIG. 3 is a photograph showing the grid crease slightly integrated in the connective tissue. The HA crystal are embedded in the surrounding connective tissue. No foreign body reaction is visible.
Figure 4:
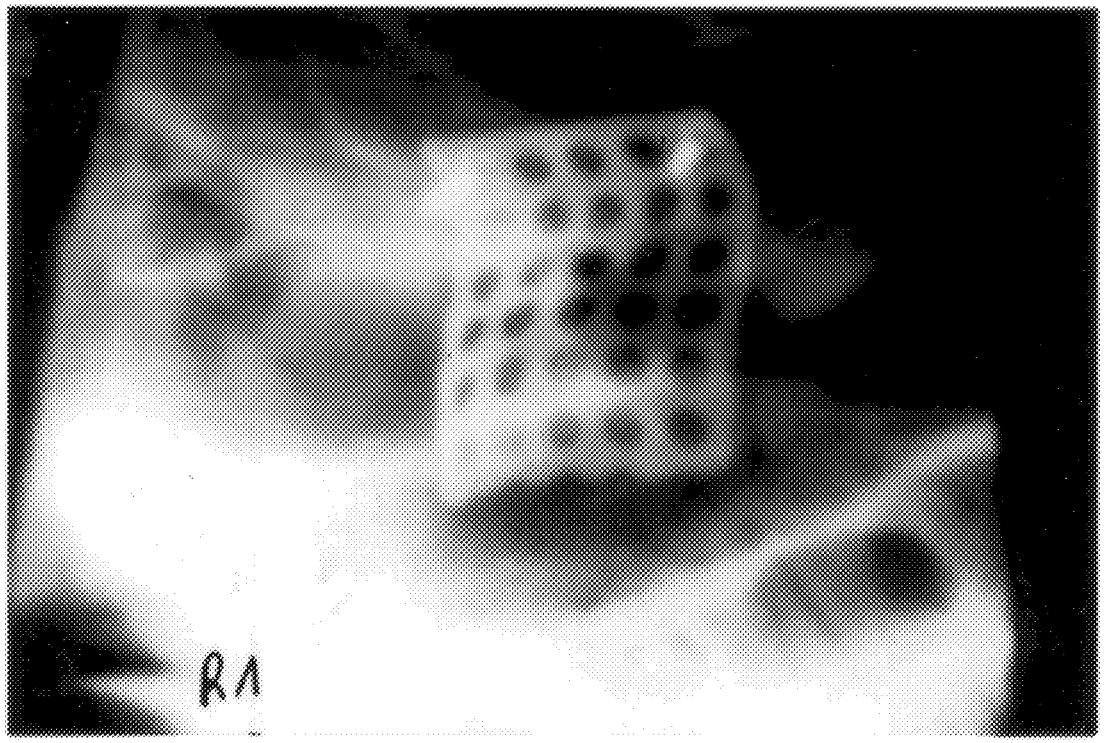
FIG. 4 is an x-ray photograph showing the screws with which the grid was affixed to the bone. It also shows the entire grid structure without bony covering. Two screws serve to affix the grip.
Figure 5:
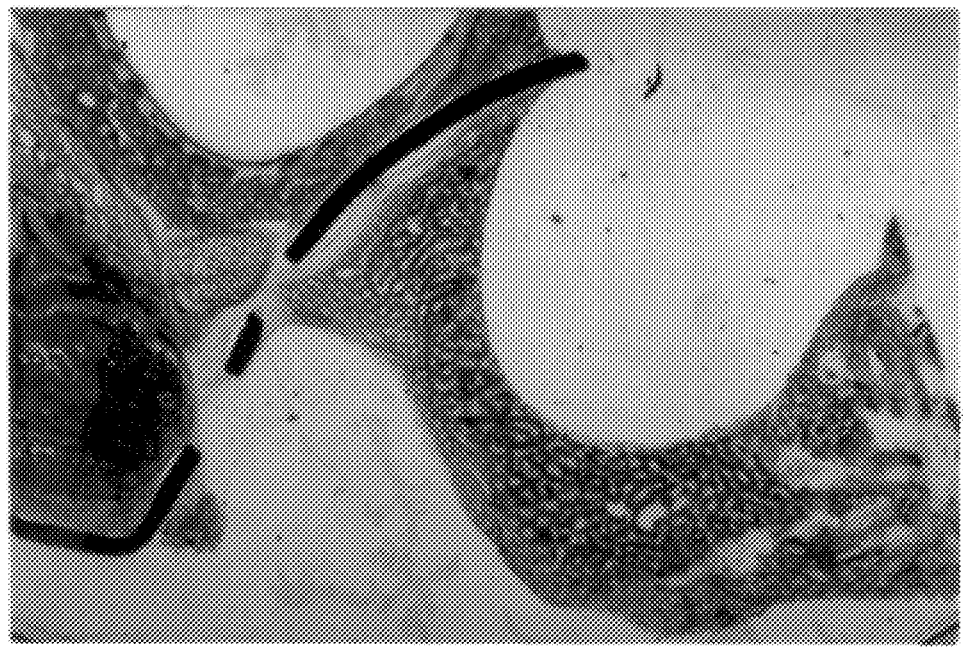
FIG. 5 is a photograph showing the rounded bone borders corresponding to normal healing approximately 8 weeks after the trauma. Also, the photograph shows the mucus membrane (blue) resting on the grip, right under the bone lamella.
Figure 6:
FIG. 6 is a photograph showing a mucus membrane of maxillary sinus, titanium grip, connective tissue (BG). The non-boned connective tissue area corresponds to the remainder of the implant BIC. In the area of the grip, still no new formation of bone.
Figure 7:
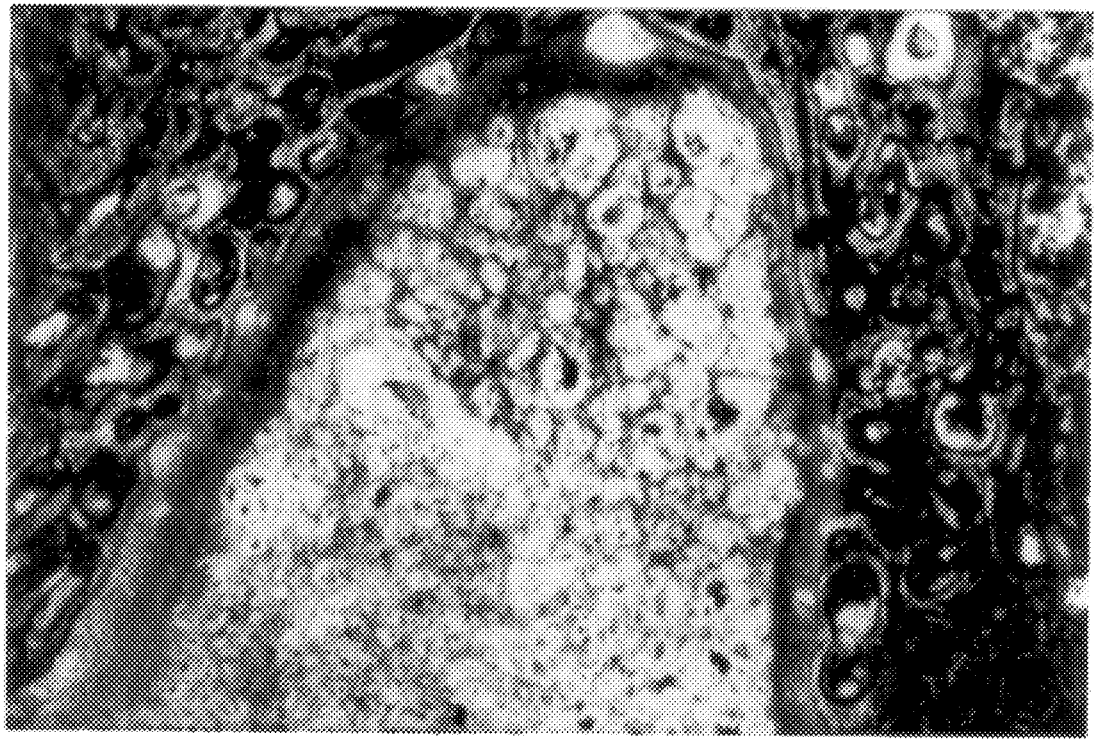
FIG. 7 is a photograph showing newly formed bone, shown as an intense blue band between the bone trabecula and BIC area. All blue structures correspond to cell nuclei with Giemsa dye. Collagen appear light red. The area of band correspond to the active bone formation zone, with preosteoblast borders and osteoblasts.
Figure 8:
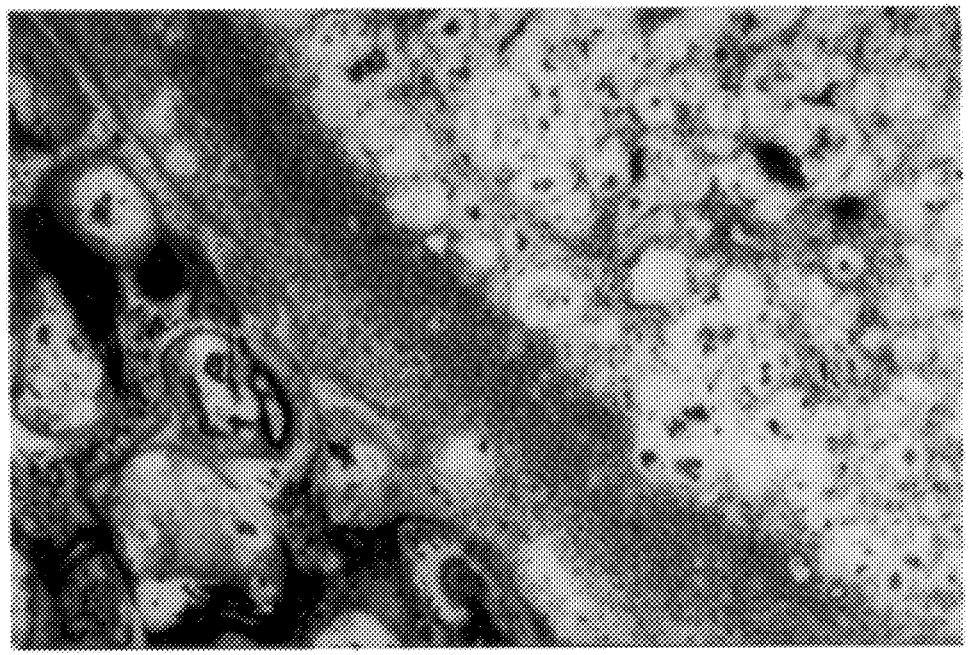
FIG. 8 is a photograph showing BIC area with collagen fibers and individual cell nuclei. A broad band of loosely assembled preosteoblasts lie adjacent to the right. These are embedded in collagenic fibers (reddish). Then there is a 1 to 2 row band of osteoblasts.
Figure 9:
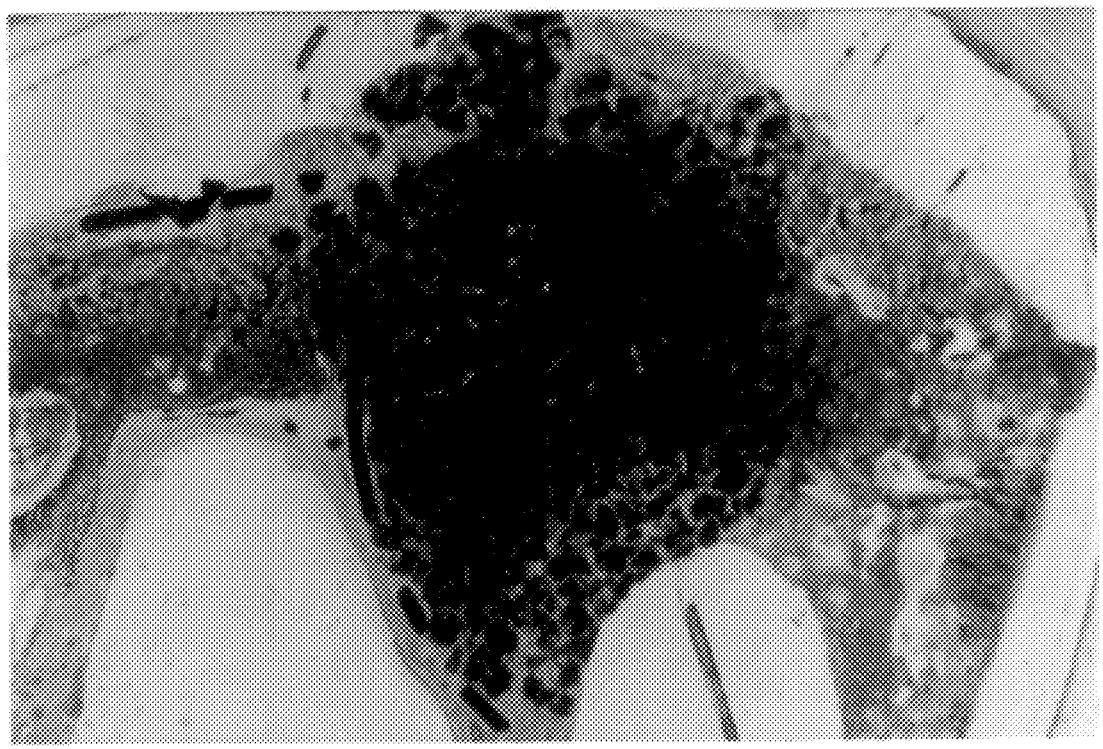
FIG. 9 is a photograph showing crystal embedded in connective tissue. Bony structures can not be recognized at this magnification.
Figure 10:
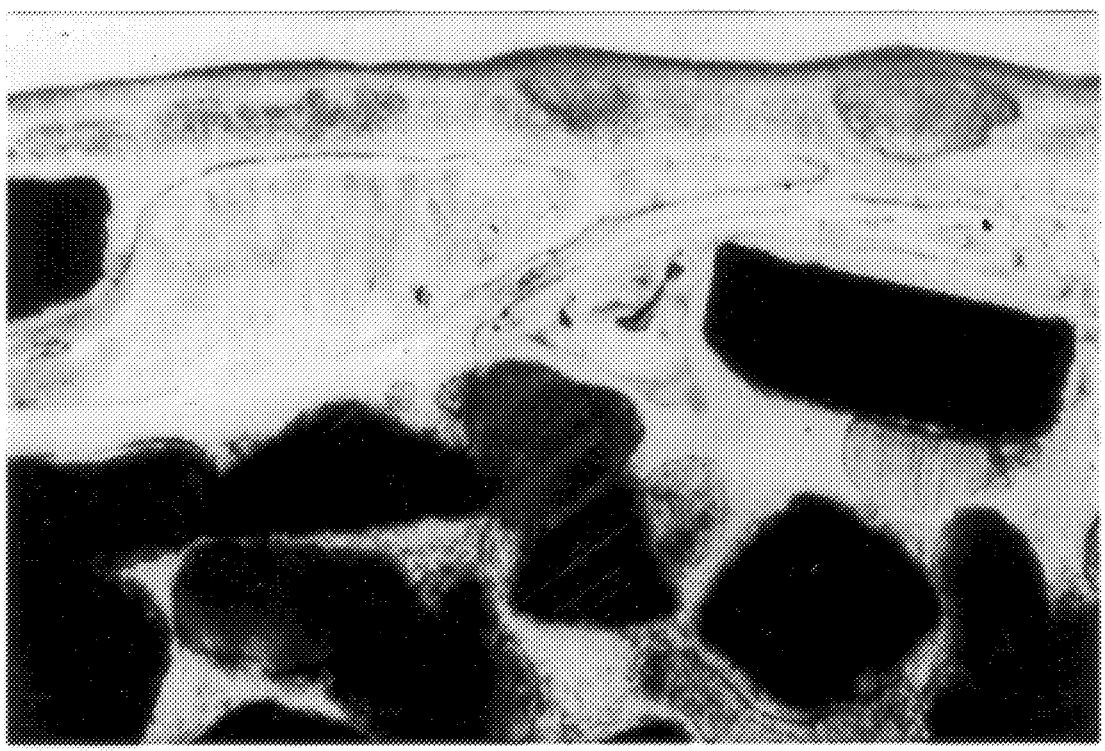
FIG. 10 is a photograph showing a magnification of a section of mucus membrane of maxillary sinus.

The following non-limitative examples are intended to illustrate the use of BIC for inducing bone growth.

EXAMPLE I

Isolation of the bone growth complex

The bone-inducing complex used in this work was isolated by the method described in my copending applications as well as the Joos et al. publication all of which are incorporated herein by reference, in their entiretie's.

The source of BIC is preferably cattle bones.

Steps for receiving BIC (abbreviated)

Freshly butchered diaphysis of a tubular bone from a calf

Milling to a particle size of <2 mm

Removal of fat in acetone

Decalcification in 0.6 N HCL

Washing and lyophilization

Demineralized bone matrix

Extraction in 4 M Gu HCL

Dialysis against distilled water

Precipitation of BIC

Fresh calf bones are cleaned of soft tissue and frozen in liquid nitrogen. In the subsequent milling process, the bone is crushed to particles >2 mm. The removal of fat in chloroform/methanol and the demineralization by means of 0.6 normal HCL follow. After subsequent freeze drying, the proteins are extracted by 4 molar guanidine hydrochloride solution. The soluble proteins are removed by dialysis against distilled water and subsequent centrifuging. The precipitated fraction obtained after dialysis of the solution of the soluble protein contain BIC and can be used as a bone-inducing implant. Thus, BIC is a complex of proteins, which cause the complete morphogenesis of bone in vivo.

After implantation in rats, an ossicle, which has a well-differentiated bone structure, develops. Mineralized lamellar bone as well as the typical marrow structures are formed. Although the individual steps of the differentiation of mesenchymal cells into osteoblasts are not known, in-vitro tests show that BIC leads to the formation of different osteoblast-specific marrows, as for example, collagen Type 1, alkaline phosphatase and osteocalcine. It was of importance that the bone-inducing effect of BIC could be blocked completely by means of TGF β antibodies.

BIC can be blocked completed by means of TGF β antibodies. Furthermore, a combination of the TGF β and the epidermal growth factor (EGF) results in a high degree of similar effect on mesenchymal cells, i.e. the cells treated in this way produced increased collagen of Type I and distinctly reduced the formation of collagen type III.

It may be assumed that BIC is comprised for the most part of collagen, bovine bone morphogenetic protein and TGF β.

A variation on this isolation method which may be employed is disclosed in my co-pending application Ser. No. 08/313,113 incorporated herein by reference.

EXAMPLE II

Use of BIC in the Maxillary Sinus

The maxillary sinus of the pig pneumaticizes the caudal portion of the os maxillary and the body of the os zyomaticum. In grown animals, it penetrates to the caudal far in the zygomatic arch. Its rostral section is formed as one unit. In the caudal area, one of the cavities is divided into a medial and a lateral sinus by a ventral high-extending arched bone lamella, which includes an ethmoid bone cell and the canalis infraorbitalis. The nervus infraorbitalis reaches through the foramen maxillary in the canalis infraorbitalis and leaves through the foramen infraorbitale, to split subsequently like a cluster. The opening to the nasal cavity lies at the height of the 6th molar; although only pea-sized in new-borns, it achieves an extent of 2–4 cm after only 8 weeks for pigs.

The animals in the first testing process were 4–5 weeks old at the time of the operation and had boy weights of between 15.1 and 22.3 kg. In the second part, older and heavier animals were used. The pigs were 8–9 weeks old and weighed 35–42 kg.

A total of 10 running pigs of a hybrid breed were used. These animals came from the "Bundes Hybridzuchtprogramm" [Federal Hybrid Breeding Program] and are as very unsusceptible to stress.

It is a matter of, without exception, of male castrated pigs. The animals in the first testing process were 4–5 weeks old at the time of the operation and had body weights of between 15.1 and 22.3 kg. In the second part, older and heavier animals were used. The pigs were 8 weeks old and weight 35–42 kg.

The housing took place in a pigsty with straw, daylight and a rubber ball as a toy. A low calorie pig feed with an energy content of 12.6 MJ/kg was used. The water was supplied ad libidum through a nipple spout. All of the animals were dewormed (Concurat from Bayer) when placed in the stall and immunized with 2 ml vaccine against swine erysipelas (Erysorb from Höchst).

To eliminate postmortem changes, an electronically readable microchip (Indexell from Rhone-Merieux) was implanted between the caudal edge of the musculus masseter and the base of the ear, in addition to ear tags.

The introduction of narcosis took place about 10 min after premedication with 2 mg Azaperon (Stresnil from Janssen) /kg body weight intramuscular and 0.05 mg Atropine /kg body weight subcutaneously at the base of the ear, with 30 mg of Katevet (from Parke-Davis) /kg body weight, likewise intramuscularly. After local anesthesia of the larynx with Gingicain spray (Höchst), the patient was intubated and connected to a narcosis machine with a half-closed system (Spiromat 650 from the Draegerwerke Lübeck). A halothane, laughing gas and oxygen mixture was used. The percentual halothane portion was between 0.8 and 1.6 volume percentage of the total gas mixture in each case. The local anesthesia of the larynx was necessary since it did not relax enough under the injected narcosis and a tube could not be inserted. After extensive cleaning and disinfection of the operation area, an infiltration anesthesia with 4 ml Ultracain DS forte (Höchst) was conducted in the area of the foramen infraorbital. The cut took place about 2 cm ventral of the lower edge of the eyelid. An S-shaped cur about 10 cm long divided the cutis, subcutis, the caudal portion of the musculus levator labia and the periost. The foramen infraorbital with the nerve infraorbital was subsequently dissected bluntly. About 2 cm caudal and 1 cm dorsal to the nerve origin point, the opening of the maxillary sinus takes place by means of a bone saw on a surface of about 2.5×1.5 cm, without damaging or even perforating the mucus membrane of the maxillary sinus. The latter was then dissected from the floor of the maxillary sinus with a so-called sinus elevator of the type that a cavity of about 1 cm is presented. This was bordered on the ventral side by the bony floor of the maxillary sinus, on the medial, rostral, caudal and dorsal sides by the mucus membrane and on the lateral side by the periost. In the first pass, the implantation of 100 mg of pure compressed BIC with a volume of 0.5 cm took place on the left side in four animals. The application took place by means of a specially prepared tuberculin spray, whose cone and top have been removed. A maxillary sinus was not augmented and thus serves as a control. In the right maxillary sinus, 66 mg of resorbable hydroxyapatite (Osteogen from Impladent LTD) was implanted in 4 animals, mixed with 33 mg BIC. A cavity was filled with 500 mg pure resorbable hydroxyapatite. Without closing the bones specially, a layered closing of the wound took place with periost/muscle sutures, subcutaneous sutures and skin sutures with continuous glovers' or quilted sutures. All sutures were completed with Vicryl (from Ethicon), 3- 0 thickness. In all the animals, a perioperative antibiotic with 5 ml Tardomycel comp. III (from Bayer) followed intramuscularly. The narcosis ended after successful operation on both sides. The animals were laid in individual stalls and left to rest for 2 hours until the reflexes returned. The first sequence marking was conducted 14 days after the operation. Calcine—20 mg per kg body weight—was applied intramuscularly at the base of the ear. At 2 week intervals, further markings with 30 mg Oxytetracycline (Terramycin 100 from Pfizer), alizarin complexon, and calcine and oxytetracycline again in the dosages noted above /kg body weight followed. The animals were killed 12 weeks after the operation, the appropriate parts of the skull were dissected, examined macroscopically and roentgenologically, then set and histologically examined. After only moderate results could be obtained in this run, the process in the second part was changed as follows. The animals were 8 to 9 weeks old, with body weights of between 35 and 42 kg.

After dissecting the mucus membrane of the maxillary sinus, this was pressed by a perforated titanium grid "igloo shaped" in the lumen of the maxillary sinus. This grid is fixed by 2 to 3 osteosynthetic screws on the dorsal edge of the bone window. The cavity formed in this way is bordered by the grid on the dorsal and medial side, the bony floor of the maxillary sinus on the ventral side and the periost on the lateral side. About 500 mg BIC was implanted in the left side in all 5 pigs, which was compressed to a volume of 3 cm. The right maxillary sinus in pig 1 served as a control, since this cavity was not filled. The remaining animals received 3 cm each of a non-resorbable hydroxyapatite. After a sequence marking was done away with, the animals were killed after 8 weeks, the dissections appropriately macroscopically examined and x-rayed, fixed and histologically examined.

After killing the animals, the parts of the skull to be examined were cut out. The connected soft tissue was removed with a bone rasp. Then followed the macroscopic judgement and the roentgenological examination. The dissections were set in 8% formalin with a pH buffer of 7.2 for four weeks. Then the cutting up of the resections with a microtome in approximately 3×3×3 cm blocks took place. The dissections processed in this way have their fat removed for a week in acetone and then dehydrated, likewise for a week, in alcohol. Then the blocks were embedded in acrylate plastic and trimmed to the exact dimensions of 3×3×3 cm. After that, the block was cut through the center. After the cut surface was polished, a object carrier was glued on with ethyl acrylate. Then 0.2 mm disks were cut off with the microtome, the rest of the block is glued once again and the cutting process repeated. These dissections were then ground down with sandpaper with grains 200 to 7000 to a thickness of 0.02 mm and subsequently dyed in accordance with Giemsa and Azan. The structures to be examined were represented as follows: Giemsa: nucleus red, cytoplasm orange, reticulin fiber blue, elastin fiber blue-red, collagen fiber blue, hyalin cartilage pale blue, muscle cell cytoplasm orange. Then the microradiological examination was conducted to depict the bony structures.

RESULTS

All 10 animals, that is 20 maxillary sinuses, could be used in the examination. Since, however, the first 5 animals were based on other test conditions with regard to the amount of BIC used as well as the operational technique, both groups must be evaluated separately. All 10 animals showed pronounced peri- and suborbicular swelling one day after the operation which, however, disappeared completely after 4 to 5 days. No indications of pain were observed. Feeding continued as usual, the vitality of the animals was undisturbed. Disturbances in the healing of the wound which could have influenced the results did not occur.

In the first 5 animals, significant bone growth which exceeded the normal healing of the defect could not be determined macroscopically or microscopically. The edges of the former bone window were rounded and smoothed. In no case was the window healed like bone. Histologically, a regular bone structure, which was to be expected 12 weeks after the operation, was evident. Foreign body megakaryoblasts could be identified in the individual cuts in the border area of the mucus membrane of the maxillary sinus and the healed bone. Differences between the individual implants BIC, HA, BIC-HA in combination could not be determined. Dyed areas could be seen by the sequence marking in the maxillary bone, but an arrangement with regard to a new formation induced by BIC or else a naturally grown bone could not be determined.

Entirely different results were achieved after the operation in the animals of the second group. Already 4 days after the operation, the "BIC side" of the animal felt hard and coarse, without being warm or painful. The macroscopic judgement of the dissection 8 weeks after the operation shows clearly a more extensively pronounced osteogenesis on the left side that was treated with BIC than on the right side treated with HA ceramic. In the control test, no new bone formation could be recognized beyond the normal healing of the wound. The titanium grids on the left side are, with the exception of animal 3, completely covered with bone when viewed from the face. Even on the portion of the grid set postoperatively extrasinusidally, which serves to affix the implant, a bone lamella up to 5 mm thick results. In contrast, the extrasinusidal portion of the titanium grid rests on the right side of the wall of the maxillary sinus without exception, as represented immediately after the operation.

The windows which resulted from the operation were massively boned on the side treated with BIC in all 5 animals. On the HA side, one recognizes partially connective tissue, partially bony healed HA granules. The consistency of this tissue is soft and has a fibro-elastic characteristic. On the control side, only a slight bony regeneration can be detected in the area of the defect, but it does not approach the expected healing. The mucus membrane of the maxillary sinus rests irritation-free on the titanium grid in all cases, viewed from the medial side. Proliferation or inflamed reaction could not be noted macroscopically in any case.

The roentgenological examination of the dissections clearly shows a pronounced bony shadow on the ventral side of the titanium grid of the maxillary sinus treated with BIC. This is absent in the control test. Massive shadows can be likewise seen in the area of the hydroxyapatite crystals on the right. These appear radiologically denser, however, than those on the BIC sides.

The histological examinations took place exclusively on thinly ground dissections. The Giemsa and Azan dyes were used as dying techniques. With the help of the overall picture, one notices on the control test a healing of the operation point, but with the formation of the defect (see Figures). The extrasinusidal as well as 30% of the intrasinusidal portion of the titanium grid are not covered with bone. A new formation of bone, which exceeds the normal healing can not be recognized.

On the sides treated with BIC, an enormous new formation of bone can be seen in all cases. With the exception of animal 3, even the extrasinusidal portion of the grid is embedded in bone. The layer thickness amounts to up to 5 mm (see Figures). A massive, spongy, largely compact, bony regeneration impresses in the operatively produced cavum which is bordered by the titanium grid on the medial side. This extends over the original extension of the lateral border of the maxillary sinus and ends to the lateral side with a relatively smooth convex surface. Before the operation, this lateral border to the maxillary sinus was concave. The peripheral area of the newly yielded bone regeneration comprises largely of thick spongiosa with a low portion of marrow, as well as compact bone. Spongiosa trabecula and the compact substance have a lamellar structure. All the regenerations have in the middle a more or less connective tissue residual defect with septa throughout. The architecture of the spongiosa trabeculae is oriented toward the central connective tissue defect.

At larger magnifications one notices that the marrow cavity walls are thickly covered with osteoblast borders. These large osteoblasts, arranged in a relay-like form, have large blue-dyed nuclei. The histological construction of the central connective tissue material allows the following structures to be recognized. The limitation to the surrounding bone takes place likewise by a dense one to two-row osteoblast border. A thicker wall of preosteoblasts lies adjacent to this.

The difference from the osteoblast border is a loose bond of these preosteoblasts. A structure containing vacuoles and dominating the defect then follows. After dying in the Azan method, one sees individual chondrones of a hyalin cartilage tissue. The individual chondrones were separated by collagenic connective tissue septa. In the edge area of individual chondrones, single ossification foci are located.

There was no evidence of irritating infiltrates, indicating foreign body reactions or other immunological tissue structures at any point. On the sides of the maxillary sinus on which the hydroxyapatite ceramic was used, irritation-free healing could be macroscopically observed in each case. The implant, comprised of compact HA ceramic (calzitite) shows an almost completely connective tissue differentiation.

Some bony integrated HA granules were found only in the edge area. In contrast to this, the porous HA ceramic (osprovit) has a significantly higher bone tendency. Although this boned area is likewise seen as peripheral, it is considerably wider than for the compact HA ceramic.

A bony structure formed in animal 3 on the HA side in the area of the intrasinusidal portion of the titanium grid. This has, however, no connection to surrounding bone tissue. This ectopic bone histologically comprises compact lamellarly differentiating reticulum bone.

The microradiological examination of the dissections shows clearly that a calcified spongy structure formed in the area of the BIC implant. In contrast, the osteointegrated porous HA granules can be distinguished from the fibrointegrated compact HA granules.

The results of the macroscopic, histological and microradiological examinations of the preparations that were obtained in this test, show that BIC is in the position to induce a new formation of bone. It should now be attempted to explain the function of BIC, better define the volume necessary for bone induction, as well as to describe other factors, which must cooperate in this.

Based on preceding tests, approximately 50 mg BIC, implanted intramuscularly, is in the position to grow an ossicle, i.e., a well differentiated bony regeneration of about 1–1.5 cm diameter. An implant quantity <10 mg does not induce osteogenesis in rat muscles. In the first run of this test, 100 mg BIC was implanted loosely in each maxillary sinus. A new formation of bone beyond the normal measure of healing could not be demonstrated in each case.

The cause for this is certainly to be found in the lacking signal effect of the implant on the inducible cell system. Furthermore, it is subject to the resorptive forces of the mucus membrane of the maxillary sinus. In particular, lymphoplasm cellular structures, in the form of lymphfollicles and individual emerging foreign body megakaryoblasts, could be seen histologically in the mucus membrane. The effect of the pressure of the mucus membrane on the implant after closing the wound and the re-aeration of the maxillary sinus support my view on this process.

Intramuscular implants also are subject to the tissue pressure. However, muscle tissue is exceptionally well supplied with blood and has cell systems which will be explained later, which promote bone formation. In particular, the resorptive properties of the musculature is obviously to be viewed as slight. Muscle tissue tends to encapsule foreign bodies such as parasitic larvae rather than resorbing them. It is also valid that if BIC were inserted in lower quantities and not pressed, then no signal effect would take place and the osteogenesis would not occur.

The 4 week long first test gave insufficient results. Bony structures cannot be sufficiently formed in less than 12 weeks because it is subject to resorption. In the second run of the test, a more stable preformed cavity was created with the help of a titanium grid. BIC was then in the position, separated from the mucus membrane of the maxillary sinus, to develop its osteoinductive potential.

The dosage of 500 mg of compressed BIC per maxillary sinus was sufficient to induce bone growth indicating that a sufficient signal effect of the implant was obtained. It has been known for a long time, that bone tissue is formed from mesenchymal cells. These cells are distributed over the entire organism. It can be experimentally demonstrated that the formation of bone begins with so-called "osteoprogenitior cells" (DOPC's) obtained from vital bone marrow.

Those mesenchymal cells which can change in response to a special irritant are called "inducible osteoprogenitior cells" (IOPC's). Skeletal muscle, soft tissue surrounding bone and of course, also periost have the largest amounts of IOPC's. These are also the areas in which bone can be formed most easily. At this point, a normal healing of the bone is described.

As a result of a bone trauma, macrophages which are chemotactically determined, wander into the wounded area. Vessels and fibroblasts sprout in. The macrophages eliminate tissue debris and possibly existing bacteria. During this, fibroblasts produce an extracellular base substance. This bonds loosely with the collagen of the bone matrix and so determines the migration and attachment of mesenchymal cells. The bone matrix affects this mitogenetically and induces its conversion into "inducible osteoprogenitior cells" and into finished osteoblasts. These produce further bone-fundamental substances as a base for a new bone. Examinations indicate a period of about 21 days was needed for this development.

BIC also works chemotactically on undifferentiated mesenchymal cells. It possesses an angiogenetic factor, thus determines the sprouting of vessels and creates the nutritive assumptions for forming bone. BIC works in particular on the pericytes of the capillaries. These are connective tissue cells, the flat cell body of which covers the surface of the capillaries and are decisively shared in the material exchange between the capillary blood and the tissue.

BIC does not work mitogenetically, but rather differentially on mesenchymal cells, that is to say, there is no increased rate of mitosis. The differentiation process ends when BIC is completely broken down (Schmidt, K. -H., Pers. Communication). The dissections obtained from this work all have a cell-free area macroscopically and histologically which is not differentiated any better, set more or less in the center, running in the direction of the grid.

Despite its structure, which has vacuoles and which remember the cartilage lacunae without anything further, no portion of such tissue could be recognized in the preparations. In the border area of new bone—BIC residual, one notices a one to two-row line of osteoblasts. A broad band of loosely attached preosteoblasts are adjacent to there. This covers the loose connective tissue without sharp delineation. These non-ossified areas permeated by connective tissue septa appear to be remainders of the compressed BIC that was implanted.

The cause for this is the low nutrition in these areas based on the vascularization that is not yet sufficient. It is to be assumed that further along this course, these areas would be changed to bone as well. It can be eliminated from this that a dismal, centrifugal ossification occurs, that is to say one that advances from the outside to the inside.

Furthermore, the parts of the periost adjacent to the operational area will have led to a periostal ossification, that is to say beginning with the bone skin. If one looks at the HA preparations, a distinct osteointegration of the crystals in the border area of the bone—hydroxyapatite is to be recognized. An osteogenetic effect, comparable with that of BIC did not occur.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed:

1. A method of stimulating the formation of new bone in a maxillary sinus of a patient comprising the steps of:

providing a bone induction complex comprising a bone derived protein complex comprising a bone derived chemotaxic component to attract bone stem cells from healthy tissue, bone derived structural and adhesive components to provide a framework to which the attracted stem cells may bind and be supported, and bone derived growth and maturation components so that the stem cells will divide and mature into osteocytes;

implanting a pharmaceutically effective amount of said complex into said maxillary sinus cavity; and permitting said bone growth to occur.

2. The method according to claim 1, wherein said complex is made by a process comprising the steps of:

detaching soft tissue from an animal bone;

removing fat, condyles and marrow from said bone;

grinding said bone;

demineralizing said ground bone to form demineralized ground bone;

adding said demineralized ground bone to an aqueous solution of a chaotropic compound to denature the proteins;

separating the soluble proteins from the insoluble residue and retaining the soluble, denatured proteins;

isolating the complex from the soluble portion by means of ultrafiltration fractionation; and renaturing the isolated complex to form the bone growth inducing complex.

3. The method according to claim 2, wherein said bone is from a calf.

4. The method according to claim 2, wherein said bone pieces are frozen in liquid nitrogen before grinding.

5. The method of claim 2 wherein ultrafiltration is performed in a flat bed or hollow-fiber system.

6. A complex for reossification in the maxillary cavity of a human made according to the method of claim 2.

7. The method according to claim 1 wherein said complex is isolated from bone by a process comprising the steps of:

detaching soft tissue from bone;

removing fat, condyles, and marrow from said bone;

grinding said bone to ground bone;

demineralizing said ground bone to form demineralized ground bone;

adding said demineralized ground bone to an aqueous solution of a chaotropic compound to denature proteins of said denatured, ground bone;

separating the soluble proteins from the insoluble residue of the solution formed from adding said demineralized ground bone to said aqueous solution of chaotropic compound, and retaining the soluble proteins;

isolating a denatured bone inducing complex from the soluble protein by means of ultra filtration fractionation; and renaturing the isolated denatured bone inducing complex then lyophilizing said bone inducing complex to form bone growth inducing complex.

8. The method according to claim 7, wherein said bone is from a calf.

9. The method according to claim 8, wherein said bone pieces are frozen in liquid nitrogen.

10. The method of claim 7 wherein ultrafiltration is performed in a flat bed or hollow-fiber system.

11. A complex for reossification in the maxillary cavity of a human made according to the method of claim 7.

* * * * *

UNITED STATES PATENT AND TRADEMARK OFFICE
CERTIFICATE OF CORRECTION

PATENT NO. : 5,830,859
DATED : November 3, 1998
INVENTOR(S) : Schmidt, Karlheinz It is certified that error appears in the above-identified patent and that said Letters Patent is hereby corrected as shown below:

Cover Page
[76] Inventor
Change "Aeussol" to --Äussere-
Change "Weitessg.12" to --Weiter Str.--

[22] Filed,
Change "Jun." to --June-

[63] Related U.S. Application Data
Delete the first occurrence of "abandoned,"
Change "844,083" to --849,083-

[56] References Cited
Change "Kszndoz" to --Hsander-

Signed and Sealed this

Nineteenth Day of June, 2001

*Attest:*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO. : 5,830,859
DATED : November 3, 1998
INVENTOR(S) : Schmidt

It is certified that error appears in the above-identified patent and that said Letters Patent is hereby corrected as shown below:

<u>Title page,</u>
Item [76] Inventor; Change "Weiter Str." (Per certificate of correction dated June 19, 2001) to -- Weiler Str.--

<u>Item [56] References Cited</u>
Change "Hsander" (Per certificate of correction dated June 19, 2001) to -- Ksander --

Signed and Sealed this

Ninth Day of October, 2001

*Attest:*

NICHOLAS P. GODICI
*Attesting Officer*     *Acting Director of the United States Patent and Trademark Office*